US00PP18789P2

(12) United States Plant Patent
Saul

(10) Patent No.: US PP18,789 P2
(45) Date of Patent: May 6, 2008

(54) *COREOPSIS* PLANT NAMED 'JETHRO TULL'

(50) Latin Name: ***Coreopsis auriculata*×*Coreopsis lanceolata***
Varietal Denomination: Jethro Tull

(75) Inventor: Robert Mark Saul, Atlanta, GA (US)

(73) Assignee: Itsaul Plants LLC, Atlanta, GA (US)

( * ) Notice: Subject to any disclaimer, the term of this patent is extended or adjusted under 35 U.S.C. 154(b) by 0 days.

(21) Appl. No.: 11/648,866

(22) Filed: Dec. 29, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent L. Bell
(74) *Attorney, Agent, or Firm*—C. A. Whealy

(57) ABSTRACT

A new and distinct cultivar of *Coreopsis* plant named 'Jethro Tull', characterized by its compact, upright, outwardly spreading and mounded plant habit; vigorous growth habit; freely basal branching habit; freely flowering habit; rotate inflorescences with tubular golden yellow-colored ray florets; and strong peduncles that hold the inflorescences above the foliar plane.

2 Drawing Sheets

Botanical designation: *Coreopsis auriculata*×*Coreopsis lanceolata.*
Cultivar denomination: 'Jethro Tull'.

BACKGROUND OF THE INVENTION

The present invention relates to a new and distinct cultivar of *Coreopsis* plant, botanically known as *Coreopsis auriculata*×*Coreopsis lanceolata,* and hereinafter referred to by the name 'Jethro Tull'.

The new *Coreopsis* originated from a cross-pollination made by the Inventor in Atlanta, Ga. in May, 2002, of the *Coreopsis auriculata* cultivar Zamfir, not patented, as the female, or seed, parent with the *Coreopsis lanceolata* cultivar Early Sunrise, not patented, as the male, or pollen, parent. The new *Coreopsis* was discovered and selected by the Inventor as a single flowering plant from the within the progeny of the stated cross-pollination grown in a controlled environment in Atlanta, Ga. in May, 2003.

Asexual reproduction of the new *Coreopsis* by vegetative cuttings in a controlled environment in Alpharetta, Ga. since July, 2003, has shown that the unique features of this new *Coreopsis* are stable and reproduced true to type in successive generations.

SUMMARY OF THE INVENTION

The cultivar Jethro Tull has not been observed under all possible environmental conditions. The phenotype may vary somewhat with variations in environment such as temperature and light intensity, without, however, any variance in genotype.

The following traits have been repeatedly observed and are determined to be the unique characteristics of 'Jethro Tull'. These characteristics in combination distinguish 'Jethro Tull' as a new and distinct cultivar of *Coreopsis:*

1. Compact, upright, outwardly spreading and mounded plant habit.
2. Vigorous growth habit.

3. Freely basal branching habit.
4. Freely flowering habit.
5. Rotate inflorescences with tubular golden yellow-colored ray florets.
6. Strong peduncles that hold the inflorescences above the foliar plane.

Plants of the new *Coreopsis* differ from plants of the female parent, the cultivar Zamfir, in the following characteristics:

1. Plants of the new *Coreopsis* are taller than plants of the cultivar Zamfir.
2. Plants of the new *Coreopsis* and the cultivar Zamfir differ in leaf shape.
3. Plants of the new *Coreopsis* have smaller inflorescences than plants of the cultivar Zamfir.
4. Inflorescences of plants of the new *Coreopsis* have more ray florets than inflorescences of plants of the cultivar Zamfir.
5. Plants of the new *Coreopsis* have longer ray florets than plants of the cultivar Zamfir.

Plants of the new *Coreopsis* differ from plants of the male parent, the cultivar Early Sunrise, in the following characteristics:

1. Plants of the new *Coreopsis* are more compact than plants of the cultivar Early Sunrise.
2. Inflorescences of plants of the new *Coreopsis* have fewer ray florets than inflorescences of plants of the cultivar Early Sunrise.
3. Ray florets of plants of the new *Coreopsis* are tubular in shape whereas ray florets of plants of the cultivar Early Sunrise are flat and not tubular in shape.

Plants of the new *Coreopsis* can be compared to plants of the *Coreopsis* cultivar Creme Brulee, disclosed in U.S. Plant Pat. No. 16,096. In side-by-side comparisons conducted in Tolar, Tex. plants of the new *Coreopsis* differed from plants of the cultivar Creme Brulee in the following characteristics:

1. Inflorescences of plants of the new *Coreopsis* had fewer ray florets than inflorescences of plants of the cultivar Creme Brulee.

2. Ray florets of plants of the new *Coreopsis* were tubular in shape whereas ray florets of plants of the cultivar Creme Brulee were flat and not tubular in shape.
3. Ray florets of plants of the new *Coreopsis* were darker yellow in color than ray florets of plants of the cultivar Creme Brulee.

BRIEF DESCRIPTION OF THE PHOTOGRAPHS

The accompanying photographs illustrate the overall appearance of the new *Coreopsis*. The photographs show the colors as true as it is reasonably possible to obtain in colored reproductions of this type. Colors in the photographs may differ slightly from the color values cited in the detailed botanical description which accurately describe the colors of the new *Coreopsis*.

The photograph on the first sheet comprises a side perspective view of a typical flowering plant of 'Jethro Tull' grown in an outdoor nursery.

The photograph on second sheet is a close-up view of typical inflorescences and leaves of 'Jethro Tull'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Atlanta, Ga. during the spring and summer in an outdoor nursery and under conditions and practices which approximate those generally used in commercial *Coreopsis* production. During the production of the plants, day temperatures ranged from about 24° C. to 27° C. and night temperatures ranged from about 16° C. to 21° C. Measurements and numerical values represent averages for typical flowering plants. Plants were about eight months old when the photographs and description were taken.

Botanical classification: *Coreopsis auriculata*×*Coreopsis lanceolata* cultivar Jethro Tull.

Parentage:

*Female parent.*—*Coreopsis auriculata* cultivar Zamfir, not patented.

*Male parent.*—*Coreopsis lanceolata* cultivar Early Sunrise, not patented.

Propagation:

*Type.*—By vegetative cuttings.

*Time to initiate roots, summer.*—About five days at 26° C.

*Time to initiate roots, winter.*—About seven days at 18° C.

*Time to produce a rooted young plant, summer.*—About three weeks at 26° C.

*Time to produce a rooted young plant, winter.*—About five weeks at 18° C.

*Root description.*—Thick, fibrous; white in color.

*Rooting habit.*—Freely branching.

Plant description:

*Plant form/growth habit.*—Compact, upright, outwardly spreading and mounding plant habit; inverted triangle; freely basal branching with dense foliage and inflorescences held above the foliage on moderately strong peduncles. Vigorous growth habit.

*Plant height.*—About 35 cm.

*Plant diameter or spread.*—About 46 cm.

*Lateral branches.*—Length: About 3 cm. Diameter: About 2 mm. Internode length: About 7 mm. Aspect: Mostly upright to slightly outwardly spreading. Strength: Strong. Texture: Smooth, glabrous. Color: Close to 144A.

Foliage description:

*Arrangement.*—Alternate, simple.

*Length.*—About 7.5 cm.

*Width.*—About 2.5 cm.

*Shape.*—Elliptic.

*Apex.*—Acute.

*Base.*—Attenuate, tapering.

*Margin.*—Entire.

*Texture, upper surface.*—Pubescent; rough.

*Texture, lower surface.*—Smooth, glabrous.

*Venation pattern.*—Pinnate.

*Color.*—Developing and fully expanded foliage, upper surface: More green than 147A; venation, similar to lamina. Developing and fully expanded foliage, lower surface: Close to 146A; venation, similar to lamina.

*Petiole length.*—About 3 cm.

*Petiole diameter.*—About 2 mm.

*Petiole texture, upper and lower surfaces.*—Smooth, glabrous.

*Petiole color, upper surface.*—Close to 146A.

*Petiole color, lower surface.*—Close to 146B.

Inflorescence description:

*Appearance.*—Rotate single inflorescence form with ray and disc florets. Inflorescences positioned above the foliage on moderately strong peduncles. Inflorescences face mostly upright. Freely flowering habit; about four to six inflorescences developing per lateral branch. Inflorescences persistent.

*Fragrance.*—Slightly fragrant.

*Time to flower.*—Under natural season conditions, plants flower from spring through the summer in Georgia.

*Post-production longevity.*—Inflorescences maintain good substance for about one weeks on the plant.

*Inflorescence bud.*—Height: About 7 mm. Diameter: About 7 mm. Shape: Globular. Color: Close to 144A.

*Inflorescence size.*—Diameter: About 5 cm. Depth (height): About 1.8 cm. Disc diameter: About 1.4 cm. Receptacle diameter: About 9 mm. Receptacle height: About 7 mm.

*Ray florets.*—Shape: Tubular, fluted towards the apex. Length: About 2.2 cm. Width, at apex: About 1 cm. Apex: Dentate. Base: Fused. Texture, upper and lower surfaces: Smooth, glabrous; satiny. Number of ray florets per inflorescence: About 18 arranged in a single whorl. Color: When opening and fully opened, outer surface: Close to 12A. When opening and fully opened, inner surface: Close to 12A to 12B.

*Disc florets.*—Shape: Tubular; apex dentate. Length: About 1 cm. Diameter, apex: About 2.5 mm. Diameter, base: About 1 mm. Number of disc florets per inflorescence: About 60. Color: Apex: Close to 17A. Mid-section: Close to 19A. Base: Close to 19C to 19D.

*Phyllaries.*—Quantity per inflorescence: About eight in a single whorl. Length: About 7 mm. Width: About 2.5 mm. Shape: Linear. Apex: Acute. Base: Fused. Margin: Entire. Texture, upper and lower surfaces: Smooth, glabrous. Color, upper surface: Close to 143A. Color, lower surface: Close to 144A.

*Peduncles.*—Length: About 9 cm. Diameter: About 2 mm. Strength: Moderately strong. Aspect: Mostly upright to about 20° from vertical. Texture: Smooth, glabrous. Color: Close to 143A.

*Reproductive organs.*—Androecium: Quantity per disc floret: One. Anther shape: Linear. Anther length: About 2 mm. Anther color: Close to 165B. Filament color: Close to 145D. Pollen amount: Scarce. Pollen color: Close to 14A. Gynoecium: Pistil length: About 8 mm. Stigma shape: Cleft. Stigma color: Close to 21A. Style length: About 6 mm. Style color: Close to 1C. Ovary color: Close to 145C to 145D.

*Seed/fruit.*—Seed and fruit production has not been observed.

Disease/pest resistance: Plants of the new *Coreopsis* have not been shown to be resistant to pathogens and pests common to *Coreopsis*.

Garden performance: Plants of the new Clematis have exhibited good tolerance to rain and wind and have been observed to tolerate temperatures from about −10° C. to about 35° C.

It is claimed:

1. A new and distinct *Coreopsis* plant named 'Jethro Tull' as illustrated and described.

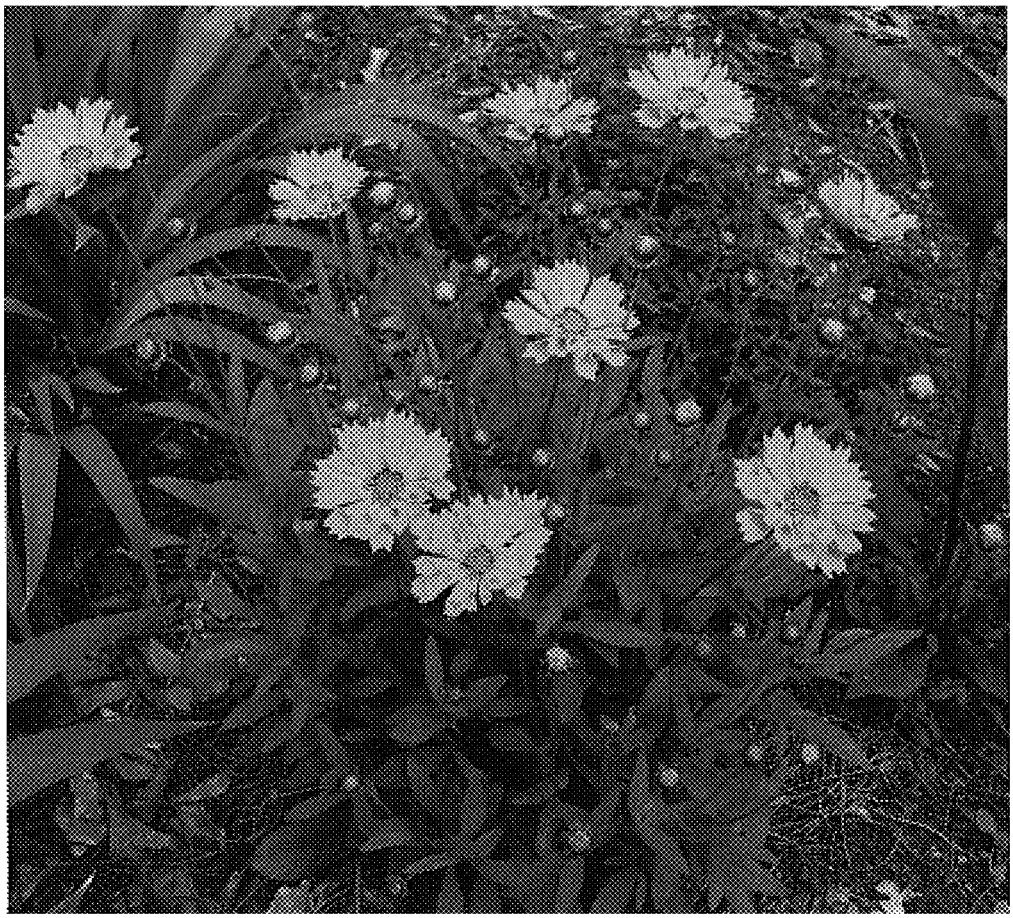

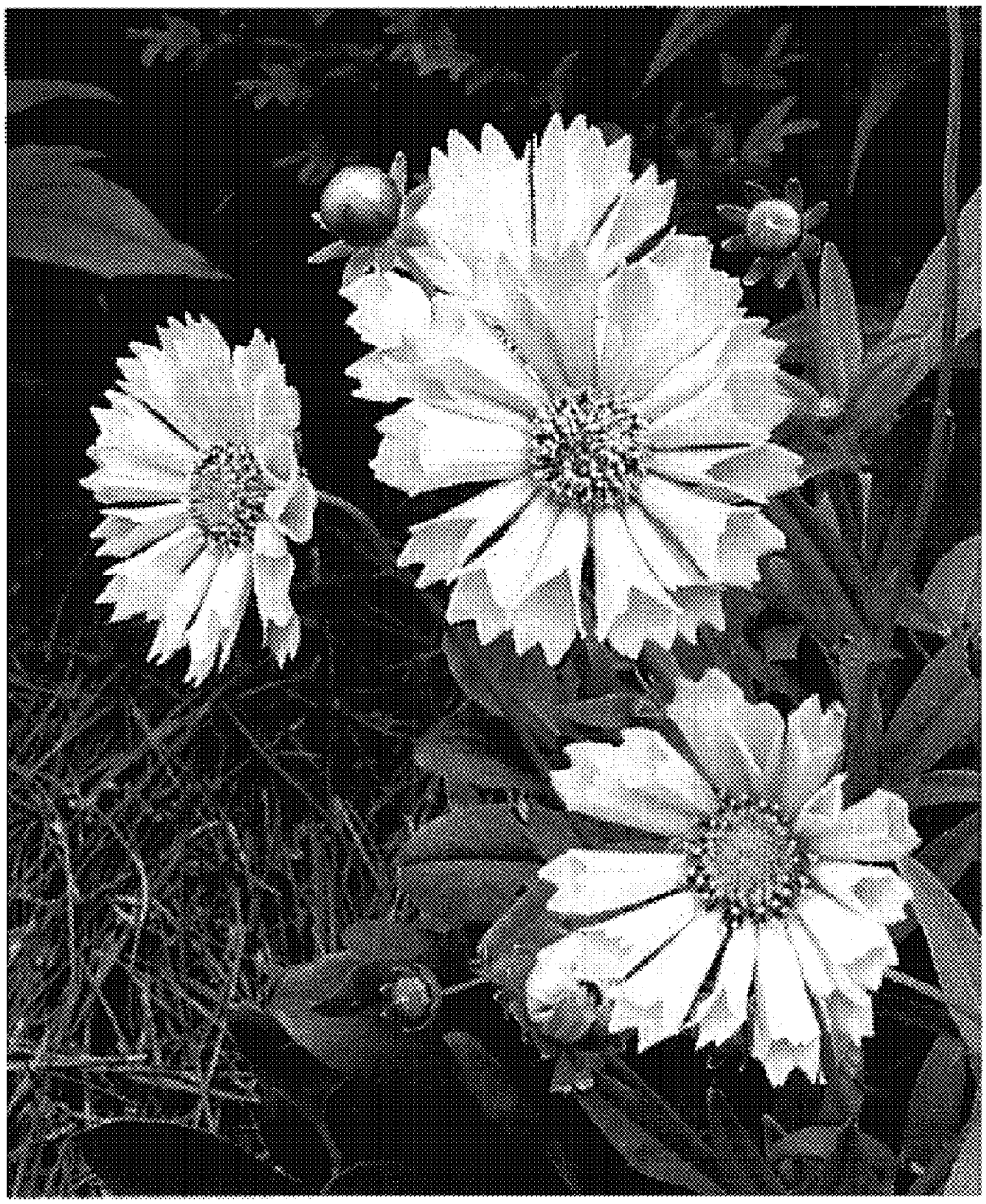

* * * * *